United States Patent [19]

Sato et al.

[11] Patent Number: 5,227,501
[45] Date of Patent: Jul. 13, 1993

[54] IODINE- AND FLUORINE-CONTAINING EPOXY COMPOUND

[75] Inventors: Shinichi Sato, Annaka; Yasuo Tarumi, Takasaki; Takashi Matsuda; Hiromasa Yamaguchi, both of Annaka, all of Japan

[73] Assignee: Shin-Etsu Chemical Co., Ltd., Tokyo, Japan

[21] Appl. No.: 882,065

[22] Filed: May 12, 1992

[30] Foreign Application Priority Data

May 14, 1991 [JP] Japan .................................. 3-138480

[51] Int. Cl.$^5$ .................. C07D 303/08; C07D 301/03
[52] U.S. Cl. ...................................... 549/550; 549/524
[58] Field of Search .................................. 549/550, 524

[56] References Cited

U.S. PATENT DOCUMENTS

| | | | |
|---|---|---|---|
| 3,358,003 | 12/1967 | Eleuterio et al. | 549/550 |
| 3,366,610 | 1/1968 | Anderson | 549/550 |
| 3,506,635 | 4/1970 | Anderson | 549/550 |
| 3,996,259 | 12/1976 | Lee et al. | 549/550 |
| 4,965,379 | 10/1990 | Ikeda et al. | 549/524 |

FOREIGN PATENT DOCUMENTS

| | | | |
|---|---|---|---|
| 49372 | 3/1983 | Japan | 549/550 |
| 2040373 | 2/1990 | Japan | 549/550 |

Primary Examiner—Joseph E. Evans
Attorney, Agent, or Firm—Wyatt, Gerber, Burke and Badie

[57] ABSTRACT

Disclosed is a novel fluorine-containing epoxide compound 6-iodo-undecafluoro-1,2-epoxy hexane which can be prepared by the epoxidation reaction of 6-iodo-undecafluoro-1-hexene with a hypochlorite such as sodium hypochlorite in a two-phase reaction system consisting of an organic phase and an aqueous phase in the presence of a quaternary ammonium compound as the catalyst.

1 Claim, 2 Drawing Sheets

IODINE- AND FLUORINE-CONTAINING EPOXY COMPOUND

BACKGROUND OF THE INVENTION

The present invention relates to a novel iodine- and fluorine-containing epoxy compound having usefulness as a crosslinking agent of rubbery elastomers and as an intermediate in the synthetic preparation of various kinds of fluorine-containing organic compounds.

SUMMARY OF THE INVENTION

The novel iodine- and fluorine-containing epoxy compound not known in the prior art nor described in any literatures and provided by the invention is 6-iodo-undecafluoro-1,2-epoxy hexane expressed by the structural formula

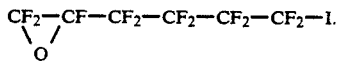

$$CF_2-CF-CF_2-CF_2-CF_2-CF_2-I. \qquad (I)$$
$$\backslash_O /$$

This compound can be prepared by the epoxidation reaction of 6-iodo-undecafluoro hexene-1 with a hypochlorite.

DETAILED DESCRIPTION OF THE PREFERRED EMBODIMENTS

Figure 1:
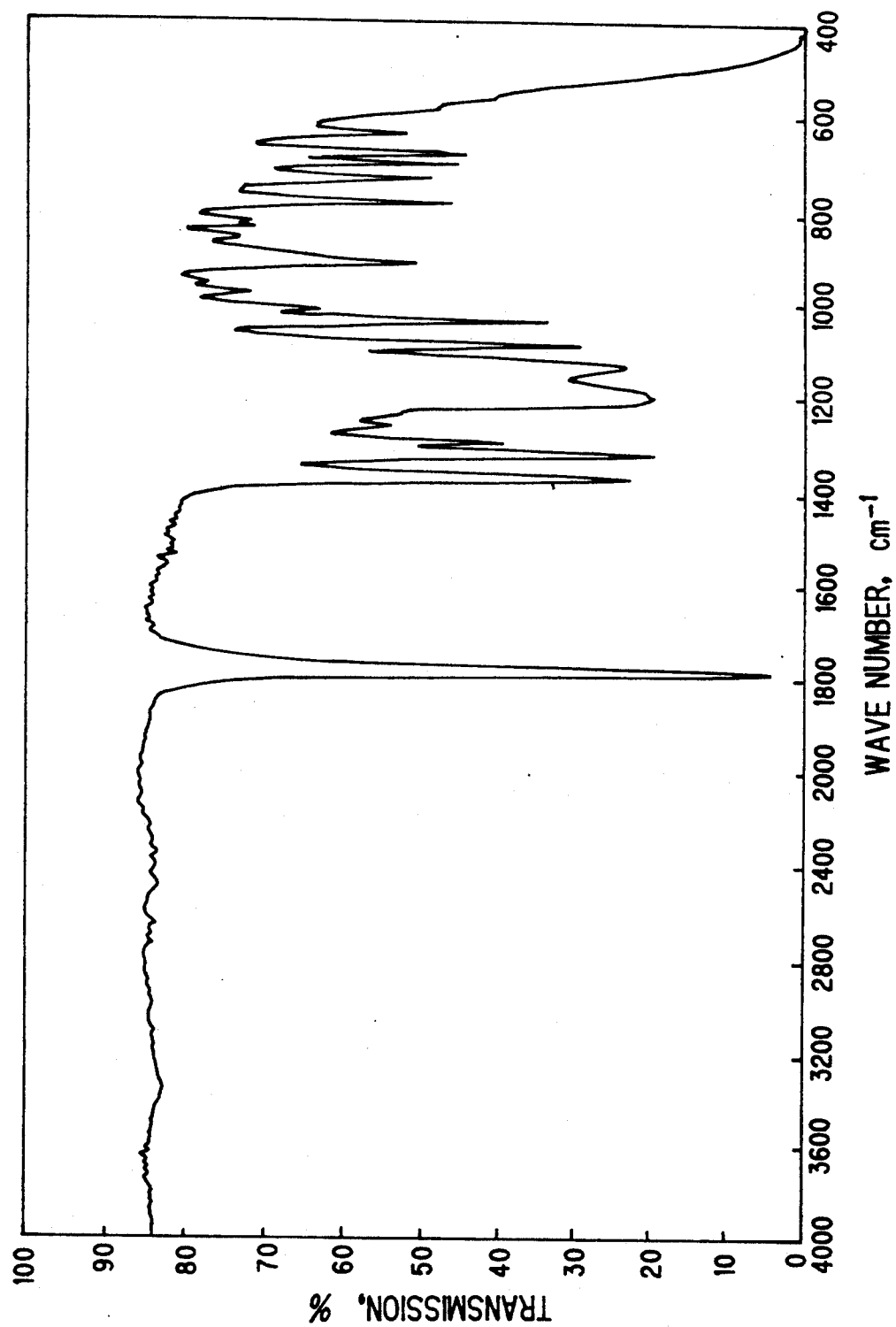
FIGS. 1 and 2 are each an infrared absorption spectrum of the starting compound 6-iodo-undecafluoro hexene-1 and inventive novel compound 6-iodo-undecafluoro-1,2-epoxy hexane, respectively.

The above described novel compound of the invention is characterized by the two types of functional groups including the epoxy groups bridging the carbon atoms having fluorine atoms at one end of the molecule and the difluoroiodomethyl group at the other end of the molecule. Several compounds are known belonging to the class of the compounds having these two types of the functional groups including 3-iodo-pentafluoro-1,2-epoxy propane disclosed in Japanese Patent Kokai 60-75472, 2,3-epoxy-pentafluoropropyl iododifluoromethyl ether disclosed in Japanese Patent Kokai 2-31716 and 3,4-epoxy-heptafluorobutyl 2-iodo-tetrafluoroethyl ether disclosed in a Russian article Zh. Org. Khim., volume 16, No. 2, pages 300–303 (1980) concerning the reactivity of cesium fluoride with an epoxy compound.

These known compounds are useful, for example, as a special crosslinking agent of rubbery elastomers or as an intermediate in the synthesis of several fluorine-containing organic compounds by virtue of the two different highly active functional groups, i.e. an epoxy group bridging carbon atoms having a fluorine atom and a difluoroiodomethyl group, at the molecular terminals although these known compounds are not without problems when they are used in the above mentioned applications.

The inventors accordingly have conducted extensive investigations for obtaining a novel compound similar to the above mentioned known compounds but more effective and free from the problems of the known compounds when it is used in the above mentioned applications arriving at a discovery that the object can well be achieved by the novel compound of the invention.

The inventive novel compound, i.e. 6-iodo-undecafluoro-1,2-epoxy hexane, can be easily prepared by the reaction of 6-iodo-undecafluoro hexene-1, which is referred to as the hexene compound hereinafter, as the starting material with a hypochlorite to effect the epoxidation reaction in a two-phase reaction medium consisting of, one, an aqueous phase and, the other, an organic phase of a water-immiscible organic solvent.

The hexene compound above mentioned is a known compound easily synthesized, for example, by the reaction of 1,2-dichloro-6-iodo-undecafluoro hexane with triphenyl phosphine.

Examples of the hypochlorite compound suitable as the epoxidizing agent include alkali metal hypochlorite such as lithium and sodium hypochlorites and alkaline earth metal hypochlorites such as magnesium and calcium hypochlorites, of which sodium hypochlorite and calcium hypochlorite are preferred for the economical reason. The hypochlorite compound is used in the form of an aqueous solution or in the form of a suspension in water. The amount of the hypochlorite compound used in the reaction is in the range from 1 to 30 moles or, preferably, from 1 to 10 moles or, more preferably, from 1 to 5 moles per mole of the hexene compound. The concentration of the aqueous solution of the hypochlorite is in the range from 0.5 to 25% by weight or, preferably, 1 to 20% by weight calculated for the content of effective chlorine. When the concentration is too low, the volume of the aqueous solution must be so large to cause a disadvantage. When the concentration is too high, the hypochlorite would be somewhat unstable due to decomposition.

Examples of the water-immiscible organic solvent include chlorinated hydrocarbon solvents such as methylene chloride, chloroform, 1,2-dichloroethane and the like, chloro-fluorinated hydrocarbon solvents such as 1,2-dichloro-1,1,2,2-tetrafluoro ethane, fluoro trichloro methane, 1,1,2-trichloro-1,2,2-trifluoro ethane and the like, perfluoro hydrocarbon solvents such as perfluoro cyclobutane and perfluoro dimethylcyclobutane, perfluoro hexane, perfluoro octane and the like. These organic solvents can be used either singly or as a mixture of two kinds or more according to need. It is important that the solubility of the hexene compound in the organic solvent is as high as possible and the solvent has miscibility with water as low as possible. In this regard, chloroform and 1,1,2-trichloro-1,2,2-trifluoro ethane are preferred as the organic solvent. The organic solvent is used in a volume in the range from 0.01 to 30 times or, preferably, from 0.05 to 20 times or, more preferably, from 0.2 to 5 times based on the volume of water forming the reaction medium.

The reaction between the hexene compound and the hypochlorite compound is promoted when the reaction is performed in the presence of a quaternary ammonium compound acting as a phase-transfer catalyst. The quaternary ammonium cation forming the quaternary ammonium compound is exemplified by tetraethyl ammonium ion, tetra-n-propyl ammonium ion, tetra-n-butyl ammonium ion, tri-n-octyl methyl ammonium ion, benzyl trimethyl ammonium ion and the like which is coupled with a counter anion such as chlorine ion, bromine ion, iodine ion, fluorine ion, sulfate ion, hydrogensulfate ion, hydroxy ion and the like, of which chlorine ion, hydrogensulfate ion and hydroxy ion are preferred. Tri-n-octyl methyl ammonium chloride is the most preferable. The quaternary ammonium compound as the catalyst is used in an amount in the range from 0.0001 to 10 moles or, preferably, from 0.001 to 1 mole per mole of the hypochlorite compound.

The reaction of the hexene compound with the hypochlorite compound is performed at a temperature in the range, usually, from −25° to 80° C. or, preferably, from −20° to 60° C. or, more preferably, from −18° to 40° C. although the reaction temperature should be high enough not to cause freezing of the reaction mixture. The reaction is complete usually within 2 hours to give the desired 6-iodo-undecafluoro-1,2-epoxy hexane in a yield of, for example, at least 50% of the theoretical value.

In the following, more detailed description is given of the synthesis and characterization of the 6-iodo-undecafluoro-1,2-epoxy hexane by way of an example.

EXAMPLE

Into a three-necked flask of 1 liter capacity equipped with a reflux condenser and thermometer were introduced 25.3 g (0.062 mole) of 6-iodo-undecafluoro hexene-1 and 125 ml of 1,1,2-trichloro-1,2,2-trifluoro ethane to form a mixture. While vigorously agitating the mixture in the flask at room temperature by means of a magnetic stirrer, 375 ml of an aqueous solution of sodium hypochlorite, of which the effective chlorine concentration was 10% by weight, and then 0.4 g of tri-n-octyl methyl ammonium chloride were added to the mixture and agitation of the mixture was further continued for additional 75 minutes at 25° C. to effect the reaction. Completion of the reaction was checked by the disappearance of the hexene compound as the starting material in the reaction mixture by the gas chromatographic analysis of the reaction mixture periodically undertaken.

After completion of the reaction, the organic solution of the reaction mixture was taken by phase separation, twice washed with water and then dehydrated by the addition of anhydrous sodium sulfate. The dehydrated reaction mixture was subjected to flash distillation and then distillation under reduced pressure to give 13.1 g of a fraction boiling at 36°–37° C. under a pressure of 34 Torr, which could be identified to be the desired 6-iodo-undecafluoro-1,2-epoxy hexane from the analytical results shown below. The yield of the product compound was about 50% of the theoretical value.

Figure 2:
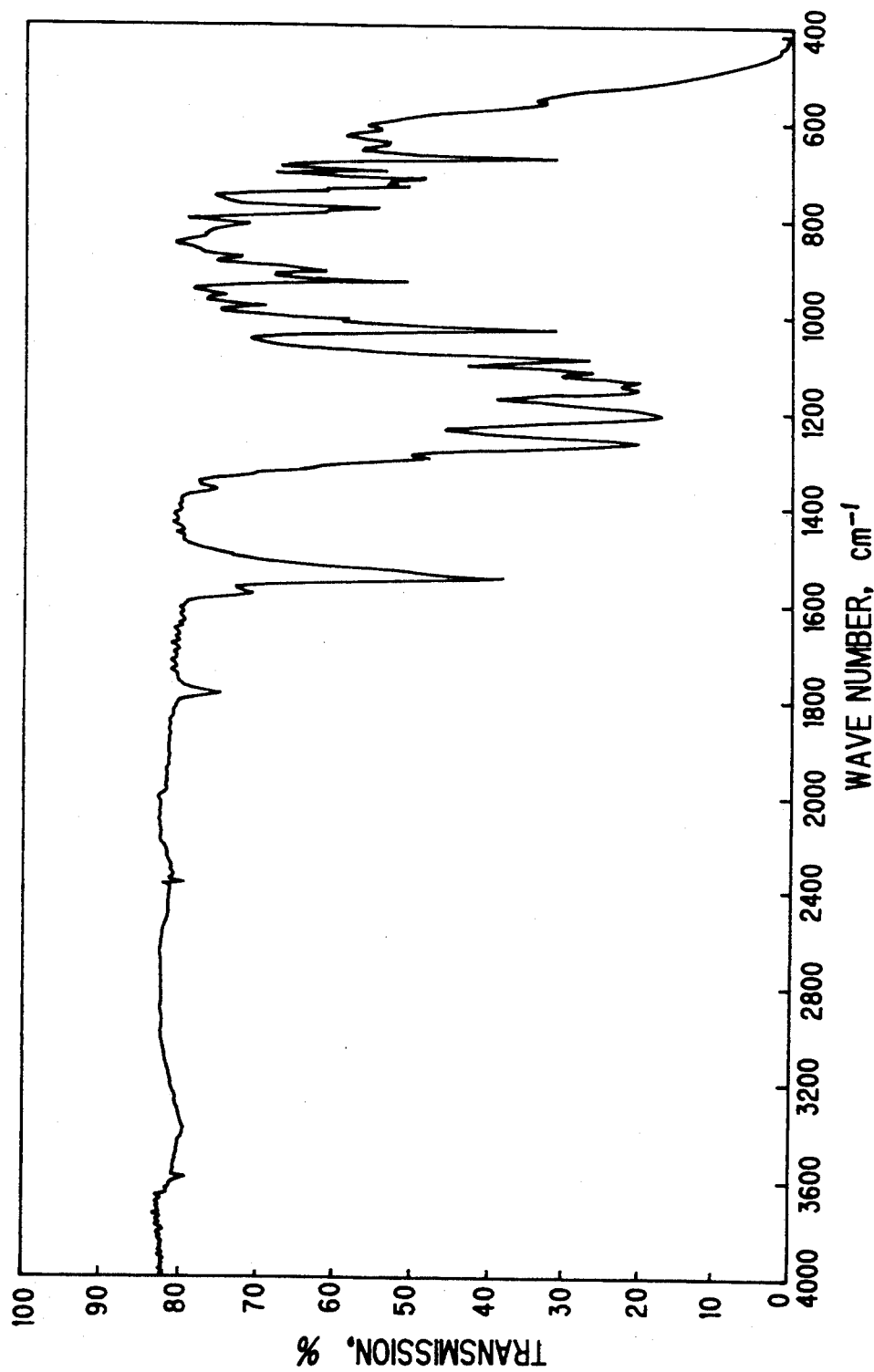

Infrared absorption spectrum (NaCl plates): FIG. 1 of the accompanying drawing shows an infrared absorption spectrum of the starting hexene compound, of which the strong absorption band at a wave number of about 1790 cm$^{-1}$ is assignable to the groups of —CF=CF$_2$ while this absorption band is not found in the spectrum of FIG. 2 which shows the spectrum of the product compound indicating a strong absorption band at a wave number of about 1540 cm$^{-1}$ assignable to the fluorine-substituted epoxide structure.

$^{19}$F-NMR analysis (CF$_3$COOH as the external standard):

| δ, ppm | structure |
| --- | --- |
| 15.6 | —C$\underline{F}_2$I |
| −34.7, −37.1 | F$_2$C——C— \\ / O |
| −38.4 | F$_2$C——CF—C$\underline{F}_2$— \\ / O |
| −46.5, −47.9 | —C$\underline{F}_2$— |
| −76.3 | F$_2$C——C$\underline{F}$— \\ / O |

Mass-spectrometric analysis: m/e(species, relative intensity) 297 (M-I, 4), 181 (12); 177 (12); 131 (32); 127 (15); 100 (15); 97 (14); 69 (100); 50 (12).

What is claimed is:

1. 6-Iodo-undecafluoro-1,2-epoxy hexane.

* * * * *